United States Patent
Weese et al.

(10) Patent No.: US 7,558,439 B2
(45) Date of Patent: Jul. 7, 2009

(54) MOTION ARTIFACT CORRECTION OF TOMOGRAPHICAL IMAGES

(75) Inventors: Jürgen Weese, Aachen (DE); Peter Roesch, Aachen (DE); Angela Jane Da Silva, Danville, CA (US); Michael J. Petrillo, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 629 days.

(21) Appl. No.: 10/520,988

(22) PCT Filed: Jul. 8, 2003

(86) PCT No.: PCT/IB03/03011

§ 371 (c)(1),
(2), (4) Date: Jan. 10, 2005

(87) PCT Pub. No.: WO2004/008390

PCT Pub. Date: Jan. 22, 2004

(65) Prior Publication Data

US 2005/0226527 A1    Oct. 13, 2005

(30) Foreign Application Priority Data

Jul. 10, 2002    (DE) ............................. 102 31 061

(51) Int. Cl.
*G06K 9/32*  (2006.01)
*A61B 5/05*  (2006.01)
(52) U.S. Cl. .................. 382/294; 600/427
(58) Field of Classification Search ........... 382/294
See application file for complete search history.

(56) References Cited

U.S. PATENT DOCUMENTS

| | | | | |
|---|---|---|---|---|
| 5,361,763 A * | 11/1994 | Kao et al. | ................. | 600/410 |
| 5,546,472 A * | 8/1996 | Levin | ................. | 382/131 |
| 5,560,360 A * | 10/1996 | Filler et al. | ................. | 600/408 |
| 5,647,360 A * | 7/1997 | Bani-Hashemi et al. | ..... | 600/425 |
| 5,690,106 A * | 11/1997 | Bani-Hashemi et al. | ..... | 600/425 |
| 5,768,413 A * | 6/1998 | Levin et al. | ................. | 382/173 |
| 5,839,440 A * | 11/1998 | Liou et al. | ................. | 600/431 |
| 5,850,486 A * | 12/1998 | Maas et al. | ................. | 382/294 |
| 5,910,728 A * | 6/1999 | Sodickson | ................. | 324/309 |
| 6,075,836 A * | 6/2000 | Ning | ................. | 378/98.12 |
| 6,088,611 A * | 7/2000 | Lauterbur et al. | ......... | 600/407 |
| 6,178,271 B1 * | 1/2001 | Maas, III | ................. | 382/294 |
| 6,229,570 B1 * | 5/2001 | Bugwadia et al. | ......... | 348/441 |
| 6,298,110 B1 * | 10/2001 | Ning | ................. | 378/4 |
| 6,341,179 B1 * | 1/2002 | Stoyle et al. | ................. | 382/254 |
| 6,490,476 B1 * | 12/2002 | Townsend et al. | ......... | 600/427 |
| 2001/0031920 A1 * | 10/2001 | Kaufman et al. | ............ | 600/431 |
| 2003/0004405 A1 * | 1/2003 | Townsend et al. | ......... | 600/407 |

OTHER PUBLICATIONS

Tom et al., Motion Estimation of Skeletonized Angiographic Images Using Elastic Registration, IEEE Transactions on Medical Imaging, vol. 13, No. 3, Nov. 1994, pp. 450-460.*

(Continued)

*Primary Examiner*—Bhavesh M Mehta
*Assistant Examiner*—David P Rashid (57) ABSTRACT method A first image of a moving object is acquired by of a first imaging method, e.g by PET or SPECT imaging. The first image contains artifacts caused by object motion. From two further images acquired by a second imaging method, e.g. C.T. or M.R., and representing the object in respective states of motion, a motion model is formed. The information contents of either the first image or a combination image, formed from the first image and the two further images, and the motion model is enhanced.

21 Claims, 5 Drawing Sheets

OTHER PUBLICATIONS

Erdi, et al.; Using Mutual Information for Automated 3D Registration in the Pelvis and Thorax Region for Radiotherapy Treatment Planning; 2000; Medical Imaging; 416-425.

Hedley, et al.; Motion Artifact Suppression: A Review of Post-Processing Techniques; MRI; 1992; 10:627-635.

Hsiao, et al.; Noise Propagation from Attenuation Correction into PET Reconstructions; 2001; IEEE, pp. 108-112.

Katsaggeios, A.K.; Iterative Image Restoration Algorithms; 1989; Optical Engineering; 28:7:735-748.

* cited by examiner

MOTION ARTIFACT CORRECTION OF TOMOGRAPHICAL IMAGES

BACKGROUND

The invention relates to a method of enhancing the information contents of an image of a moving object. The invention also relates to a system in which a method of this kind is carried out as well as to a computer program enabling a data processing unit to carry out such a method. This method is used notably in the field of medical imaging systems.

A method of this kind is applied wherever images of a moving object are to be formed, which images often contain unavoidable motion artifacts. As a result, the object is usually imaged in a blurred fashion so that it offers a viewer only inadequate information concerning the object. Motion artifacts often give rise to unusable images in particular in the case of slice images or volume images of a moving object.

The article by D. Mattes et al. "Nonrigid multimodality image registration", Medical imaging 2001: Image Processing, Proceedings of SPE vol. 4322 (2001), discloses a method in which an image of a moving object, acquired and reconstructed by means of the PET method and containing motion artifacts, is superposed on a further image of the moving object, acquired and reconstructed by means of the CT method, so as to form a combination image. The combination image is formed by special registration of the two individual images while utilizing pregnant, bilateral similarity information contained in both images. Because of the physical circumstances, the PET image contains pronounced motion artifacts which are not taken into account in the disclosed method and give rise to problems during the registration.

SUMMARY

It is an object of the invention to increase the information content of images containing motion artifacts.

This object is achieved in accordance with the invention by means of a method of enhancing the information contents which can be derived from a first image, containing motion artifacts, of a moving object, which method includes the following steps:

a. using two further images which represent the object in a respective state of motion with as few motion artifacts as possible, b. determining a motion model which characterizes states of motion assumed by the object while performing the motion between the two states of motion.

The first image may have to be reconstructed from projections.

There is a first image of a moving object which contains motion artifacts which are due to the motion of the object. Motion artifacts are the cause, for example, that the object is imaged less sharply as the object has moved more during the acquisition time. Such motion artifacts may occur when the acquisition time of the imaging method used for the acquisition is long in comparison with the motion, so that the object moves during the acquisition. The term "motion" is to be interpreted in a very broad sense. The object may perform, for example, a very complex natural motion (human heart) or merely a linear, uniform motion (a sphere rolling at a constant speed).

Furthermore, at least two further images of the object are involved. Each of these images represents a respective state of motion of the object and is as free from motional artifacts as possible, the two states of motions originating from the motion performed by the object during the acquisition of the first image. Alternatively, the two states of motions represented may also originate from a motion which has been performed by the object at a different instant and is at least approximately the same as the motion performed by the object during the acquisition of the first image. In order to image the states of motion with as few artifacts as possible, the acquisition time is generally short in comparison with the duration of the motion.

The imaging methods that can be used for the acquisition of the first image and the two further images may be the same or be different. When a common imaging method is used for all images, the different characteristics of the first image and of the two further images can be realized by way of different adjustments of acquisition parameters. When two different imaging methods are used, each of which reproduces other characteristics of the object, information of such different characteristics can be advantageously supplemented at a later stage.

There is also determined a motion model of the motion of the object which characterizes states of motion assumed by the object while performing the motion between the two states of motion. In particular in the case of a complex natural motion of the object, individual parts of the object move differently during the execution of the motion; for example, some parts of the object travel only a short distance whereas other parts follow a long and possibly curved path. Starting from of one of the two states of motion, the motion model describes the behavior for different parts of the object during the motion from one state of motion to the other.

The information thus obtained as regards the motion of the object can be incorporated in various ways in supplementary image processing or image forming steps, resulting in a higher quality of the resultant images.

For example, such supplementary steps in accordance with the invention as disclosed in claim 1 are:

c. forming an intermediate image of the object from the motion model and the two further images, the intermediate image representing the object at least approximately as if it had performed the motion, d. forming a combination image from the intermediate image and the first image.

The intermediate image formed represents the object as if it were to perform the motion. To this end, starting from the two known states of motion, the object motion is imitated by means of the motion model and the intermediate image is formed from this information, for example, by superposition. The intermediate image thus reconstructed represents the object with substantially the same motion artifacts as the first image.

A viewer may wish to view the first image with as few falsifications as possible, despite the motion artifacts contained therein, because information may be lost in the course of known image processing methods. The superposition of the intermediate image and the first image so as to form a combination image then offers the advantage that on the one hand the first image is presented with as few falsifications as possible whereas on the other hand the information from the two further images is prepared in the intermediate image in such a manner that it can be combined directly with the information of the first image.

The combination can be carried out in a variety of manners. For example, the two images can be additively superposed, so that the relevant information of the individual images is represented in an overall image. The variable division of the combination image constitutes a further possibility, a part of the combination image then being represented by the intermediate image whereas the other part is represented by the first image. A viewer can then move the boundary between the two sub-regions, so that an object detail is represented once by the intermediate image and once by the first image. Alternatively, the sub-regions can also be displayed so as to be separated by a window, the window being displaceable across the combination image by means of a control unit. A simple method of forming the combination image consists in arranging the intermediate image and the first image adjacent one another so that the two images are simultaneously presented to the viewer.

A further supplementary step in accordance with claim 2 consists of:

c. focusing the first image by means of the motion model.

During the focusing the motion artifacts are reduced to such an extent that the object represented in the first image is presented sharply to a viewer. Generally speaking, the object appears to be unsharp to a viewer because several states of motion of the object motion are represented in superposed form in an image. For the focusing of an object represented with motional unsharpness, the object is represented in only one state of motion of the motion in that the superposition with the remaining states of motion is eliminated. This is possible when the motion leading to the unsharp representation is known. The motion model of the object motion determined in the first step contains exactly this information concerning the object motion, and a focusing algorithm can utilize information from the motion model for focusing. This results in an image which represents the object in one state of motion (that is sharply) and appears to the viewer as if it has been acquired by means of the first imaging method. This is advantageous in particular when the first imaging method is not suitable, for example, for physical reasons, to acquire a sharp image of the moving object.

When the first image is to be reconstructed from projections, in conformity with claim 3 there are the following supplementary steps:

c. forming an intermediate image of the object from the motion model and the two further images, the intermediate image representing the object at least substantially as if it had performed the motion, d. reconstructing the first image from the projections of the object and the intermediate image.

For this method to be used it is necessary that, instead of a first image, projections of the moving object are available first and that the first image is reconstructed from these projections, for example, by means of a data processing unit. Methods of this kind are known inter alia from the field of medical slice or volume imaging, such as computed tomography, magnetic resonance tomography or positron emission tomography.

In particular in the case of radiation-emitting object, as used for imaging in the case of positron emission tomography, the fact must be taken into account that a part of this radiation is absorbed by other parts of the object. Methods are known which take into account information concerning such so-called location-specific attenuation for the reconstruction in order to avoid artifacts in the reconstructed image. To this end, usually a transmission image of the object if formed, which transmission image represents the necessary location-specific attenuations. It is a drawback, however, inter alia that the motions of the object, leading to artifacts in the first image, are not or not adequately present in the transmission image so that they cannot be taken into account for the reconstruction. This leads to artifacts in the reconstructed image.

From two points of view it is particularly advantageous to utilize the intermediate image during the reconstruction: on the one hand, the intermediate image contains the necessary information for location-specific attenuation and on the other hand the motion of the object, being present in the intermediate image, is taken into account. The images reconstructed with the aid of such an intermediate image have an enhanced quality in comparison with images reconstructed by means of conventional transmission images. Therefore, the intermediate image should generally contain information concerning the formation of the image by means of the first imaging method, in this case being information as regards the location-specific attenuation.

It is to be noted that in particular the methods in conformity with the claims 1 and 3 or the claims 2 and 3 can be combined and that they advantageously supplement one another.

In particular in the case of objects whose parts move differently the representation by way of motion vector fields in conformity with claim 4 offers a simple and adequate location-specific representation of the necessary information for the remainder of the method. A motion vector field indicates how or along which path the corresponding part of an object moves while performing the motion between the two known states of motion.

When it is known how often the relevant states of motion are assumed by the object while performing the motion, or how long the relative stay is of the object in the relevant state of motion, the generating of the intermediate image is particularly simple in conformity with claim 5. Such information can be based, for example, on a model of the motion or be determined by means of a sensor while the motion is performed. Such formation of the intermediate image offers the advantage that it is not necessary to describe the entire motion in the motion model, but only information concerning individual states of motion as well as their frequency.

Because of the use of different imaging methods it may occur that the individual parts of the object in the intermediate image are differently localized relative to the first image. Relative differences between the object parts themselves as well as absolute differences relative to the image edges or ratio of dimensions of the object parts may then occur. In other words, the object is represented in the intermediate image with a co-ordinate system which differs from that in the first image. The registration as disclosed in claim 6 enables the relevant parts of the object to be transformed either from the positions represented in the intermediate image to the positions represented in the first image or vice versa. All parts of the object are then in the same image positions in the intermediate image as well as in the first image, thus enabling superposition of the two images.

An additional step in accordance with the invention enables the object represented in the combination image to be represented in a selected state of motion of the motion. To this end, known focusing algorithms are used in combination with the motion model and/or one of the two further images. The state of motion then represented can correspond, in conformity with the focusing algorithm used, any state of motion of the motion, but notably the states of motion represented in the two further images.

An advantageous further version of the method of claim 2 is disclosed in claim 8. A viewer is not only offered the sharper first image, but additionally a comparison with one of the two further images is made possible.

The method in accordance with the invention can in principle be carried out by means of two imaging methods which are based on the same modality. As opposed thereto, the use of different modalities enables the representation of different characteristics of the moving object in the corresponding images. The method in accordance with the invention is advantageously used in conformity with claim 9 when the first imaging method cannot offer images of a moving object without motion artifacts.

The object is also achieved by means of the system as disclosed in claim 10. An image processing system is to be understood to mean any system capable of receiving the images or the data formed by the method in accordance with the invention, of processing these images or data accordingly, and of either visualizing the result or applying it to other systems. The image processing system may be completely independent from the devices acquiring the image data by means of the relevant imaging methods. On the other hand it is also feasible to construct the image processing system as a component of a larger system. The data processing unit may optionally be constructed so as to be programmable.

The object is also achieved by means of an examination system as disclosed in claim 11. The devices for forming the images are well known from prior art so that they will not be elaborated herein. By way of example there may be mentioned: X-ray systems, magnetic resonance tomography apparatus and apparatus from the field of nuclear medicine. The two imaging methods may be realized by means of a common modality of by means of different modalities. The difference will be illustrated on the basis of the following example: a common modality is assumed to be a conventional X-ray fluoroscopy where the first imaging method produces images containing motion artifacts during a long acquisition time and with a low dose, and the second imaging method produces images during a short acquisition time and with a higher dose. Depending on the construction of the examination apparatus, the two imaging methods can be carried out by means of the same device by variation of the relevant parameters. When different modalities are used, one device may be, for example, a computed tomography apparatus and the other device a PET system.

If the data processing unit of a system as described above is constructed so as to be programmable, a computer program as disclosed in claim 12 enables the data processing unit to carry out a method in accordance with the invention. Depending on the configuration, the computer program can be made available to the data processing unit by means of a computer program product such as an external, portable storage medium.

BRIEF DESCRIPTION OF THE DRAWINGS

The following examples and embodiments are illustrated with reference to the FIGS. 1 to 6. Therein

FIGS. 1 to 3 show the steps of a number of versions of the method in accordance with the invention. The rectangular boxes represent results, data, images etc. Steps of the methods are stated within an ellipse.

DETAILED DESCRIPTION

Figure 1:
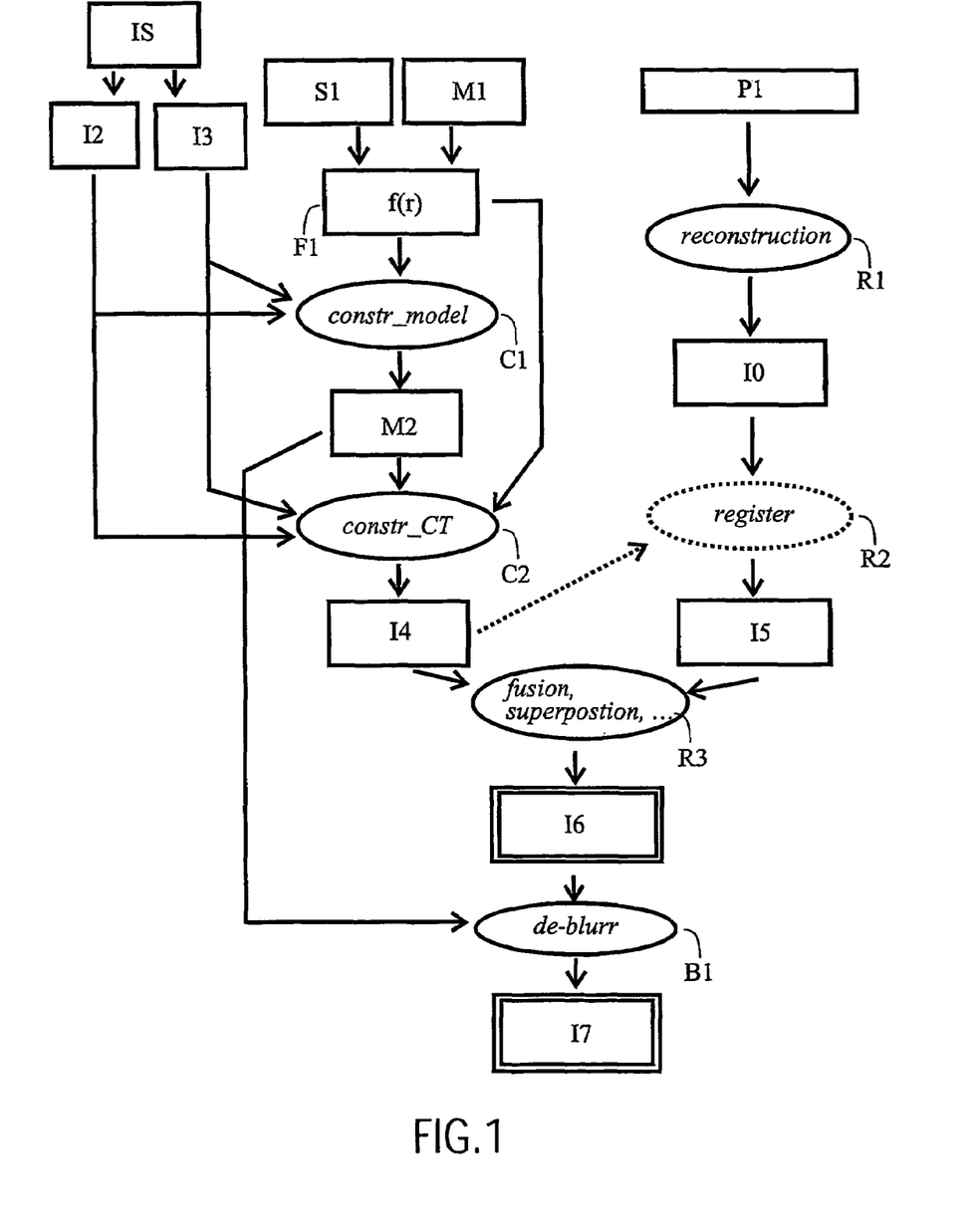
FIG. 1 shows the block diagram of a version of the method in conformity with claim 1.

FIG. 1 is a diagrammatic representation of the steps and results of a first version of the method. It is an object of the method to acquire images of a moving object by means of two different imaging methods, in this case being methods based on PET and CT. The different imaging methods enable different information to be acquired as regards the moving object. Such different information is to be presented in common to a user.

Projections P1 which have been made, for example, of the thorax of a patient at the area of the diaphragm by means of the PET (Positron Emission Tomography) method are available (the method itself is not shown in FIG. 1). The PET method is known from the field of nuclear medicine and is intended for the formation of slice images or volume images. A metabolic preparation, marked with given, unstable nuclides, is then injected into a patient, said preparation being taken up in a tissue-specific or function-specific manner. The radio nuclides used decay, giving rise to two $\gamma$ quanta in different successive processes in the vicinity of the location of decay, which quanta take off in exactly opposite directions, leave the patient and can be detected by suitable sensors which are arranged in a detector in the form of a ring around the patient. On their travel from their location of origin to their point of emergence from the patient the $\gamma$ quanta traverse further tissue of the patient which can absorb the $\gamma$ quanta more or less as a function of the type of tissue. Generally speaking, the $\gamma$ quanta are attenuated in a tissue-specific manner. The whole of detected $\gamma$ quanta forms a set of projections P1 of the object wherefrom a slice image or volume image can be reconstructed in known manner during a subsequent reconstruction. The PET method yields functional images of the object.

During the acquisition of the projections P1, which may last from a few minutes to one hour, the patient performs a respiratory motion during which the diaphragm moves in conformity with the respiration. This respiratory motion causes motion artefacts in the reconstructed PET image I0, said artifacts becoming manifest as an unsharp and blurred image of the object. At least two causes of such motion artifacts are known:

1) Because of the respiratory motion, a given location of a tissue occupies different positions relative to the detector, so that $\gamma$ quanta arising at this location are acquired by different sensors of the detector.

2) $\gamma$ quanta which successively arise in substantially the same location are attenuated to a different extent, because the relative position of the surrounding tissue, which is responsible for the attenuation, changes relative to the location of origin of the X-ray quanta due to the respiratory motion.

Also available are the images I2 and I3 which have been acquired by means of the CT-based method which is not shown in FIG. 1. The CT (Computed Tomography) method is known, for example, from the medical field and serves to form slice images and volume images of objects or patients, such images containing anatomical information. A CT-based system will be described in detail hereinafter. As opposed to PET images, CT images contain substantially fewer or no motion artifacts, because the image acquisition can take place substantially faster in relation to the motion. Known systems, combining PET images with functional information on the object and CT images with anatomical information on the object, ignore the motion artifacts of the PET images upon combination of the information, so that the combined information includes further artifacts or errors. These artifacts or errors are significantly reduced by means of the invention. In the further course of this description it will be demonstrated how artifacts which arise in the PET image due to the above cause 1) are taken into account in the combined information.

Figure 6:
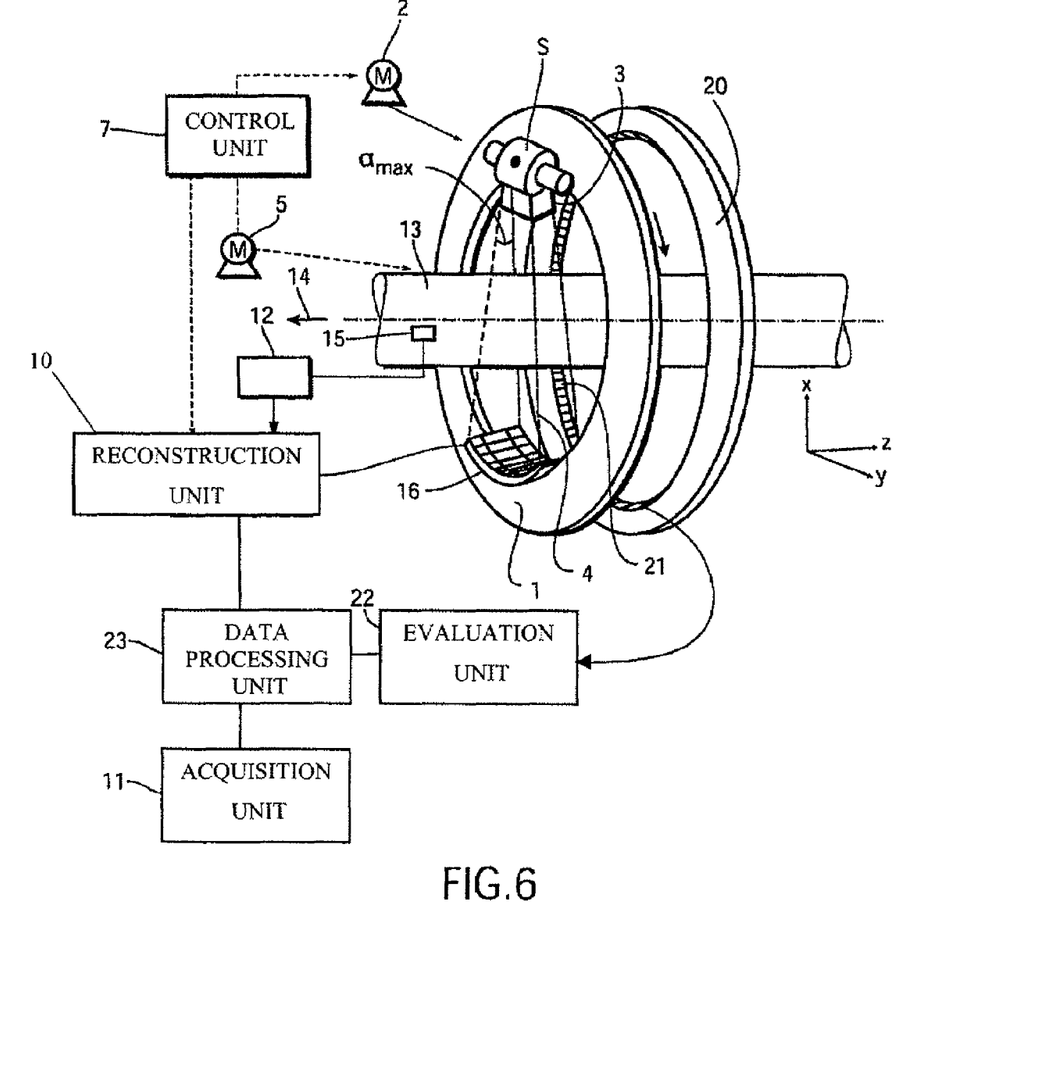
FIG. 6 shows a PET-CT combination system.

In order to illustrate the acquisition of such images, FIG. 6 shows, by way of example, a combination system which consists of a computed tomography apparatus and a PET system. The computed tomography apparatus and the PET system are both configured in principle as independent systems which, however, are geometrically coupled relative to a common axis of reference. For the image acquisition the systems are usually used consecutively; for example, first CT images, representing two striking states of motion, are acquired and subsequently the acquisition of the PET data takes place.

The computed tomography apparatus includes a gantry 1 which is capable of rotation around an axis of rotation 14 which extends parallel to the z direction. To this end, the gantry 1 is driven at a preferably constant but adjustable angular speed by a motor 2. A radiation source S, for example, an X-ray tube, is attached to the gantry 1. The radiation source is provided with a collimator arrangement 3 which forms a conical radiation beam 4 from the radiation produced by the radiation source S. The radiation beam 4 penetrates a moving object (not shown) which is present in a cylindrical examination zone 13. After having traversed the examination zone 13, the X-ray beam 4 is incident on a two-dimensional detector unit 16 attached to the gantry 1.

The angle of aperture $\alpha_{max}$ of the radiation beam 4 (the angle of aperture is defined as the angle enclosed by a ray of the beam 4 which is situated at the edge in the x-y plane relative to a plane defined by the radiation source S and the axis of rotation 14) then determines the diameter of the examination zone 13 within which the object to be examined must be present during the acquisition of the measuring values. In order to generate volume images of the object, the object which is arranged, for example, on a table in the examination zone 13, can be displaced parallel to the direction of the axis of rotation 14 or the z axis by means of a motor 5. The measuring data acquired by the detector unit 16 is applied to a reconstruction unit 10 which reconstructs therefrom the absorption distribution in the part of the examination zone 13 which is covered by the radiation beam 4. The two motors 2 and 5, the reconstruction unit 10, the radiation source S and the transfer of the measuring data from the detector unit 16 to the reconstruction unit 10 are controlled by means of a suitable control unit 7.

The motors 2 and 5 can be controlled in such a manner that the ratio of the speed of propagation of the examination zone 13 to the angular velocity of the gantry 1 is constant, so that the radiation source S and the examination zone 13 move along a helical path, that is, the so-called trajectory, relative to one another. In this case it is irrelevant whether the scanning unit, consisting of the radiation source S and the detector unit 16, or the examination zone 13 performs the rotary motion or the propagation motion, because only the relative motion is of importance. The object is not displaced for the formation of slice images.

A motion signal is derived by means of an acquisition unit 12 and a motion sensor 15 which is arranged on the object in order to detect the object motion. This signal can be applied, if desired, to the reconstruction unit 10 in order to facilitate the selection of the measuring data that is suitable for the reconstruction. Furthermore, the motion signal is used (as will be described in detail hereinafter) in accordance with the invention for the determination of the motion model.

Furthermore, a PET acquisition unit 20 is arranged so as to be concentric with relative to the axis of rotation 14; this unit is arranged as a ring around the object which is present in the examination zone 13. The acquisition unit 20 comprises individual sensors 21 which detect the γ quanta emitted by the object. In order to form slice images, it suffices to configure the PET acquisition unit so as to be quasi two-dimensional by arranging sensors 21 adjacent one another in a ring-like configuration. In order to generate volume images, the PET acquisition unit comprises a plurality of such rings of sensor which are arranged so as to be parallel to one another and around the axis of rotation 13. The signals detected by the sensors 21 are applied to an evaluation unit 22 which forms one or more PET images therefrom by means of known algorithms.

In addition to the above-mentioned functions, the control unit 7 is also arranged to displace the object between the acquisition positions of the CT system as well as those of the PET system. After successful acquisition of the CT data, for example, the object on the table is displaced, by means of the control unit 7 and the motor 5, to the acquisition position of the PET acquisition unit 20 in which the relevant preparation is injected into the object and the PET data is acquired.

The data processing unit 23 is arranged to combine, using the method in accordance with the invention as well as the motion signal, the information contents of the CT images and the PET images, to reduce motion artifacts, if any, and to visualize the results accordingly by means of a display apparatus 11. If the data processing unit is constructed so as to be programmable, it is enabled by a computer program to carry out the method in accordance with the invention. The computer program may be stored in an internal memory such as, for example, a ROM or an EPROM, or in a computer program product such as a disc or CD-ROM provided with the computer program.

The computed tomography apparatus shown as well as the PET acquisition unit may be configured in such a manner that slice as well as volume images can be acquired.

The images I2 and I3 of FIG. 1 represent two different states of motion of the motion performed by the object during the acquisition of the projections P1. Because it is inherent of the method of CT-based acquisition that significantly less time is required than for acquisition on the basis of PET, instantaneous images can be formed of the respiratory motion of the patient, notably the image I2 of the inhaled state and the image I3 of the exhaled state. The inhaled as well as the exhaled state of motion of the patient represents a particularly characteristic state of the respiratory motion. Alternatively, a sequence of CT images IS of the respiratory motion can be acquired during which the object performs the same motion as during the acquisition of the projections P1. Subsequently, using known methods, the two images I2 and I3 are extracted from the sequence IS. This offers the advantage that the motion more accurately corresponds to the motion performed by the object during the acquisition of the projections P1. When the images I2 and I3 are acquired directly, often unnatural or cramped states of motion occur in the patient; such states are not the same as those occurring during the natural respiratory motion.

Figure 4:
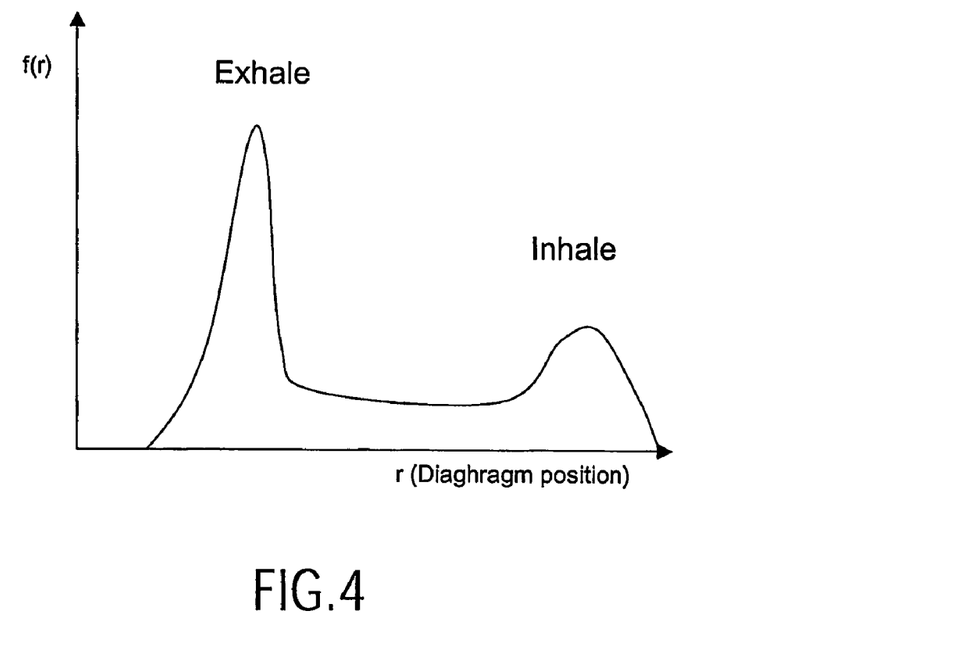
FIG. 4 shows, by way of example, the states of motion of human respiration.

From these state of motion images I2 and I3 an object motion model M2 is formed in the step C1 in combination with a state of motion function F1. A state of motion function F1 of this kind is shown in FIG. 4, by way of example, as a frequency function f(r) for the human respiratory motion. The y axis of the frequency function f(r) describes how often the relevant states of motion are assumed by the object while it performs the motion. The x axis represents successive states of motion r assumed while the motion is performed. In other words, the frequency function describes how long on average the object stays in a given state of motion in relation to the other states of motion while the object performs the motion. If the representation is normalized, the integral over this curve produces exactly 1. It is a particularly significant aspect that during the respiratory motion the organs or tissue involved in the respiratory motion remain particularly frequently or long in the exhaled state (exhalation). If merely the frequency is of interest for the further steps of the method, the order of the states of motion assumed while the object performs the motion can be ignored and the states of motion which are plotted on the x axis need not necessarily succeed one another during the execution of the motion.

Alternatively it is also feasible to utilize a motion state function F1 which not only provides information as regards the frequency of the assumed states of motion, but also describes the overall motion process (states of motion as well as their frequency and completion in time). Because such a state of motion function is redundant for the use in the next steps of this version, however, it suffices to utilize a frequency function as described above.

For known motion processes the state of motion function F1 can be derived from a function model M1 without taking into account the actual motion. This is possible notably when in most objects a motion process is very similar or the same. For example, when in the case of a human respiratory motion the model M1 is formed by the frequency function f(r) of FIG. 1, it can be considered directly as the state of motion function F1 and be used for determining the motion model M2. Alternatively, the actual motion process can be determined by means of an appropriate sensor S1. In the case of the respiratory motion, for example, the respiratory motion is determined during the acquisition of the PET projections P1 by means of a respiratory motion sensor provided on the patient and therefrom the frequency function f(r) or, more generally, a state of motion function F1 is derived for the construction of the motion model M2.

In the step C1 a motion model M2 is derived from the images I2 and I3 and the state of motion function F1. Each of the images I2 and I3 represents a respective known state of motion of the object, said states of motion also being present in the state of motion function F1. Assuming that all components of the object move locally linearly during the motion process, that is, along straight paths of different direction and length, between the states of motion shown in the images I2 and I3, for each pixel represented in one of the images I2 or I3 or for each object component the execution of the motion can be determined by means of the state of motion function F1. This location-specific motion process can be retained in a motion vector field and constitutes, in conjunction with the state of motion function F1, the motion model M2. A motion vector thus indicates the direction in which and the speed at which or the distance over which a pixel or an object component moves during the execution of the motion between each time two states of motion.

Figure 5:
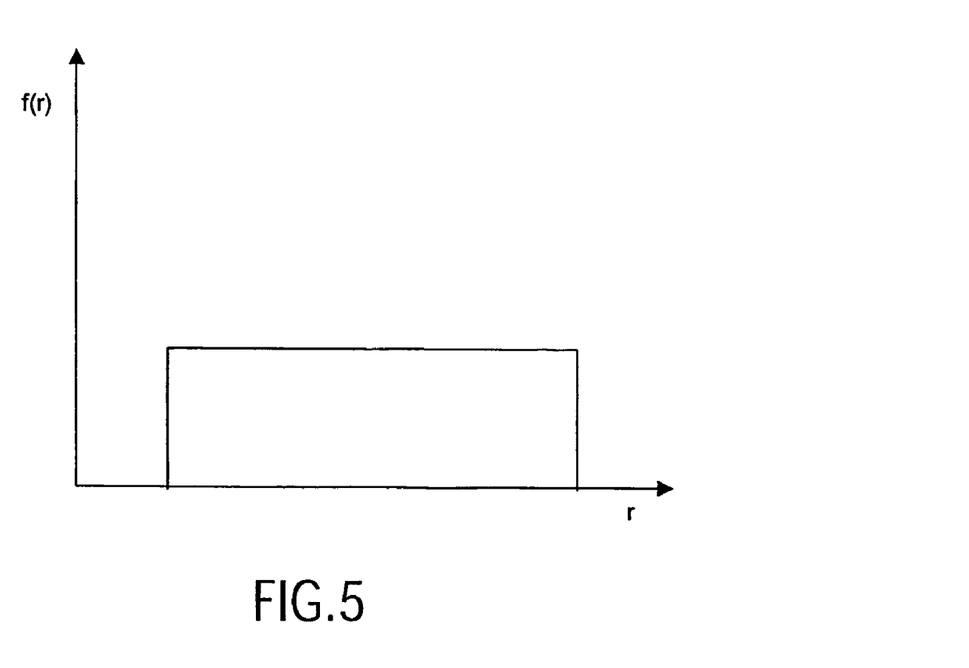
FIG. 5 shows the state of motion function of a uniform motion.

Mathematically speaking, a vector field of this kind can be described as $\vec{x}_2 = \vec{x}_3 + \vec{m}(\vec{x}_3)$. A point $\vec{x}_3$ moves towards the point $\vec{x}_2$ during the execution of the motion; the motion is characterized by the motion vector field $\vec{m}(\vec{x}_3)$ and each state of motion can be approximated by $\vec{x}(r) = \vec{x}_3 + r\vec{m}(\vec{x}_3)$. The parameter r∈[0,1] represents for r=0 the state of motion represented in the image I3, where $\vec{x}(r=0) = \vec{x}_3$ and for r=1 the state of motion $\vec{x}(r=1) = \vec{x}_2$ shown in the image I2. For the human respiratory motion, for example, $\vec{x}_3$ describes the exhaled state and $\vec{x}_2$ describes the inhaled state. Generally speaking, such a mathematical description can also be applied to a variety of other motions. The motion need not be inherently periodic and be repeated. FIG. 5 shows the frequency function of a motion of an object in which all states of motion are equally frequently assumed during the execution of the motion. This is the case, for example, for the motion where all parts of the object move in the same direction at a constant speed (for example, a bicycle rider).

The next step C2 aims to form from the images I2 and I3 an image I4 which exhibits substantially the same motion artifacts as the image I0. This is achieved in that, starting from one of the images I2 or I3, first artificial images of the remaining states of motion are formed by means of the motion model M2, said artificial images then being superposed so as to form the image I4:

$$I4(\vec{x}) = \int_0^1 f(r)I3(\vec{x}_3 + r\vec{m}(\vec{x}_3))dr.$$

The image I4 is formed from the integral over all states of motion r of the product of the image I3 and the motion vector field $(\vec{x}_3 + \vec{m}(\vec{x}_3))$ weighted by the frequency function f(r), the motion vector field $(\vec{x}_3 + \vec{m}(\vec{x}_3))$ and the frequency function f(r) constituting the motion model M2. As a result, the image I4 represents a superposition of all states of motion weighted by the relevant duration of stay.

Analogously, a theoretical consideration of the formation of the PET image I0 leads to the result that the PET image I0 also constitutes a superposition of all states of motion weighted by the relevant duration of stay; this means that it is also formed from the integral over all states of motion r of the product of an image I0a (not shown in this case) of an initial state of motion, the frequency function f(r) and the motion model $(\vec{x}_a + \vec{m}(\vec{x}_a))$:

$$I0(\vec{x}) = \int_0^1 f(r)I0_a(\vec{x}_a + r\vec{m}(\vec{x}_a))dr.$$

In the ideal case the image I0a represents the same state of motion as the image I3 and the vectors $\vec{x}_a$ and $\vec{x}_3$ as well as the relevant frequency function and the motion model correspond. This consideration of the formation of the image I0 is used in the focusing step described hereinafter, because the appearance of the motion artifacts in the image I0 is thus substantiated.

As an alternative for a combination apparatus as shown in FIG. 6, the images I0 as well as the images I2 and I3 can be acquired by means of two independent systems. The object is then positioned in the first apparatus, for example, the PET system, and the PET image is acquired. Subsequently, the object is positioned in the second system and the CT images are acquired. Because of the local separation of the two systems, the object components in the PET image I0 usually are localized differently from those in the CT images I2, I3 and I4, so that only an inadequate direct superposition or direct comparison of the images I4 and I0 can be performed. Therefore, in a step R2 a so-called registration operation is performed. The step R2 is optional and is not necessary when the co-ordinate system of the images I0 suitably accurately corresponds to that of the images I2 and I3 (as is the case in the system shown in FIG. 6). I0 can then be equalized with I5 and the method can be continued as described hereinafter.

Registration is a generally known method of equalizing co-ordinate systems between two or more images with corresponding structures; a physical correspondence of two identical objects of different contents may then also occur. This is the case, for example, for a functional PET image and an anatomical CT image of the same object. After successful registration, the object parts represented in one image can be associated with the corresponding object parts in the other image by the co-ordinate transformation determined. As a result, for example, the object parts shown in one image can be shifted in such a manner that they occupy the corresponding positions of the identical object parts represented in the other image.

The article by D. Mattes et al. "Nonrigid multimodality image registration", Medical Imaging 2001: Image Processing, Proceedings of SPIE Vol. 4322 (2001) describes how such a registration of a CT image and a PET image can be carried out. Because the registration is generally known, it will not be further elaborated herein. It is to be noted, however, that in order to facilitate the registration in known PET systems, a transmission image is acquired in addition to the actual PET image as is also mentioned in the cited article. Prior to the injection of the metabolic preparation marked with nuclides, a radioactive source is displaced along a trajectory around the patient for this purpose, said source emitting rays in the direction of the patient which penetrate the patient and are detected by sensors of the PET detector which are situated opposite the radiation source. The transmission image subsequently reconstructed is in principle similar to a CT image and, because of the anatomical information contained therein, is better suitable for registration with the CT image, notably in the case of a poor image quality of the actual PET image. When the co-ordinate transformation between the transmission image and the CT image has been determined, the co-ordinates of the actual PET image and the CT image can be made to correspond, because the co-ordinate systems of the transmission image and the PET image are substantially identical. This method is not shown in FIG. 1, but can nevertheless be used herein.

After successful registration R2, the pixels or the object components of the image I0 can be transformed in the co-ordinate system of the image I4. This produces the PET image I5. A possible alternative, that is, transforming the image I4 into the co-ordinate system of the image I0, will not be elaborated herein. A comparison or a combination of the images I4 and I5 can now be performed, because both images exhibit substantially the same motion artifacts of the object motion and both images represent the object in relation to the same co-ordinate system. A viewer, for example, a physician, may desire the presentation of the image I0 without falsifications (a co-ordinate transformation in this sense does not represent a falsification) for given applications so as to enable comparison or combination of information therefrom with information from other images. Prior art merely offers the possibility of comparing or combining only one of the two images I2 or I3 directly with the image I0. As opposed to the image I0, the images I2 or I3 do not exhibit motion artifacts, so that on the one hand the searching of a suitable co-ordinate transformation is more difficult and on the other hand the combination or comparison itself is possible only with difficulty.

Such comparisons or combinations as shown as the step R3 in FIG. 1 are known in principle and can be realized, for example, by superposition, by adjacently arranged images, by partial superposition with manually selectable boundaries or by partial imaging of one image in the other image with manually selectable boundaries. The result of the step R3 constitutes the image I6.

In dependence on the relevant application, it may be useful for a user of the system to limit the image I6 to given information or to highlight given information in particular. To this end, an optional step B1 can be performed for focusing the image I6 which contains artifacts and in which only one state of motion of the motion is represented. A known algorithm for focusing which is suitable for linear motions is described in the article by A. K. Katsaggelos "Iterative image restoration algorithms", OPTICAL ENGINEERING, July 1989, Vol. 28, No. 7, p. 735 ff. Notably the equation (1) shows how motional unsharpness can in general be expressed by modeling the motion to a linear motion and be compensated in the further course of the method.

Figure 2:
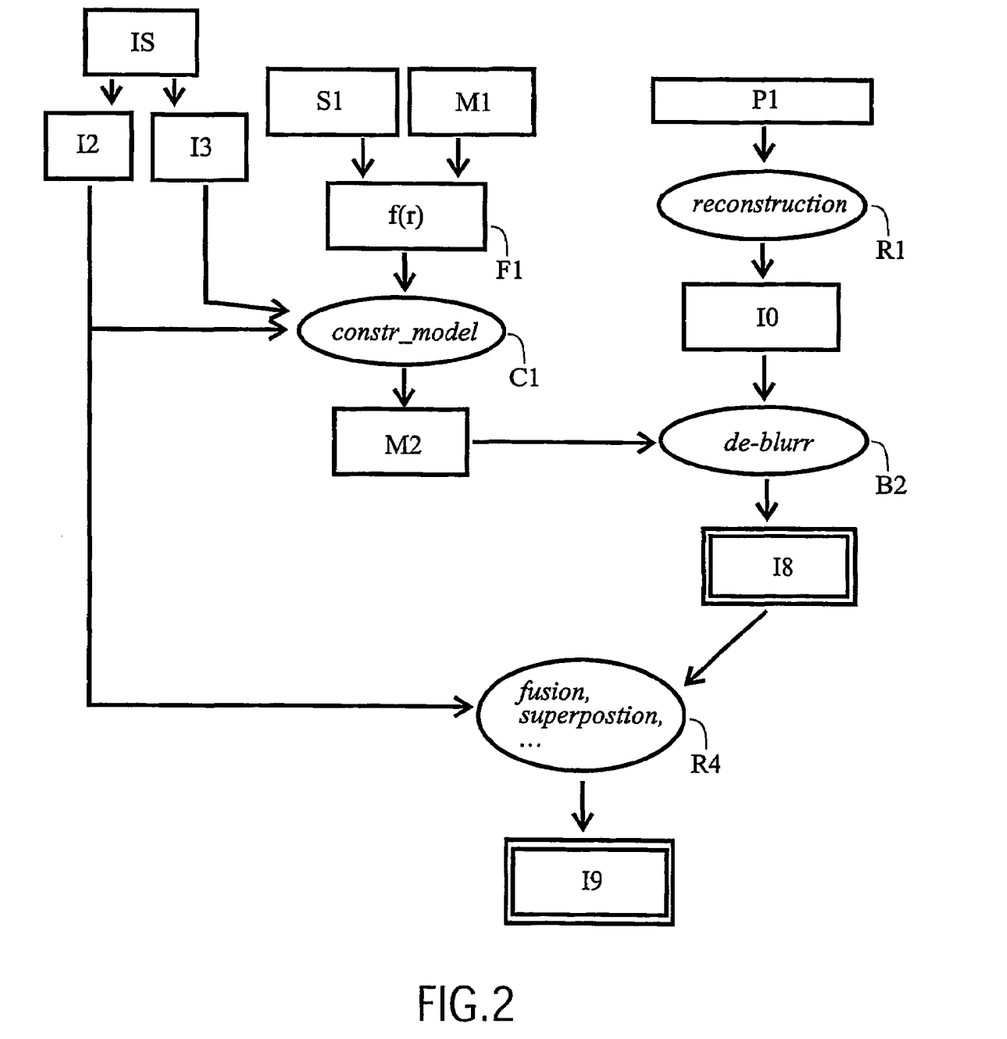
FIG. 2 shows the block diagram of a version of the method in conformity with claim 2.

FIG. 2 shows a further version of the method in accordance with the invention in a combination system. As in FIG. 1, again a motion model M2 is determined and also a PET image I0 is formed. The registration R2 shown in FIG. 1 is dispensed with, because the correspondence of the co-ordinate systems of the images I0, I2 and I3 is adequate.

In a step B2, analogous to the step B1 of FIG. 1, focusing of the image I0 is carried out. As opposed to the focusing in FIG. 1, the focusing B2 of FIG. 2 is carried out in such a manner that the sharper PET image I8 represents the same state of motion as an acquired CT image, in this case the image I2. As a result, the image I8 can be compared or combined directly with an original CT image, in this case being the image I2. Alternatively, this process can also be carried out by means of the image I3 or an image from the image sequence IS. In the comparison step R4 the same methods are used as described with reference to FIG. 1, step R3. The image I9 is the resultant image.

An alternative for the method of FIG. 2 (not shown) is to apply the focusing B1 to the image I5 instead of to the combination image I6 in FIG. 1 when the co-ordinate systems of the image I0 and the images I2 and I3 are different. As a result of the previously executed registration R2 it is first achieved that the co-ordinate system of the image I5 corresponds to that of the image I4 and hence to that of the motion model M2. This enables focusing B1 of the image I5 by means of the motion model M2. The resultant image is a PET image which represents a state of motion of the motion and contains practically no motion artifacts.

Figure 3:
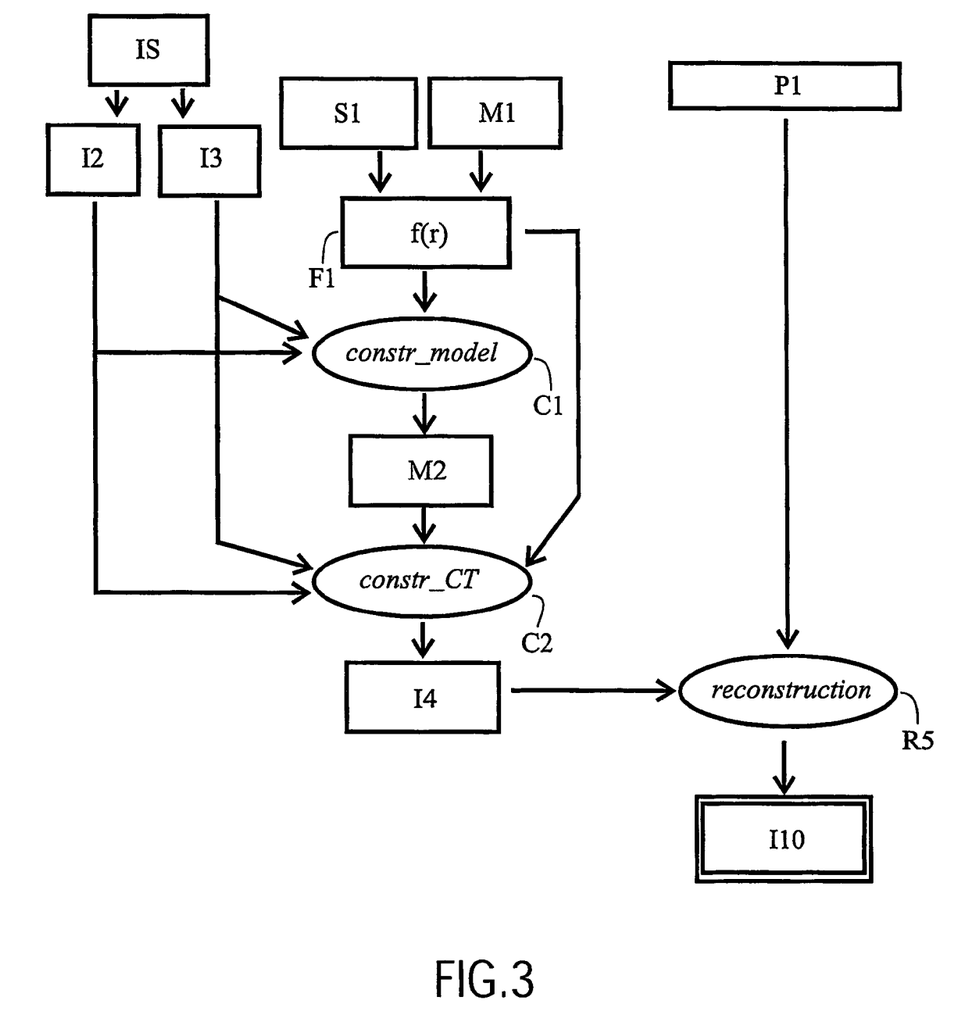
FIG. 3 shows the block diagram of a version of the method in conformity with claim 3.

FIG. 3 shows a further possibility for enhancing the information contents of an image by means of the motion model. In known PET systems a transmission image is acquired by means of the above method, that is, in addition to the actual PET image. This transmission image represents the location-specific attenuation of the radioactive radiation. This attenuation information is used for the reconstruction R1 of the projections P1 in order to correct the absorption of γ quanta by surrounding tissue (attenuation correction). In the article by I. T. Hsiao et al. "Noise Propagation from Attenuation Correction into PET Reconstructions" (published in "Nuclear Science & Medical Imaging including Nuclear Power Systems, 2000 Symposium", IEEE, ISBN 0-7803-6503-8) various methods are disclosed, for example, in Table 1, for the correction of the location-specific attenuation. Equation (4) reveals a possibility for multiplying the reconstruction, expressed as a linear reconstruction operator, by the location-specific attenuation information while taking into account distribution effects.

These methods, however, have the drawback that the transmission image, as opposed to the actual PET image, often contains only few or even no motion artifacts, because the acquisition time is short in comparison with the duration of the motion. As a result, the attenuation information is not appropriately used and the motion artifacts in the PET image, due to the above-mentioned cause 2, are not taken into account.

Therefore, in accordance with the invention the reconstruction R5 of the PET image I10 utilizes a transmission image I4 which is formed, as in FIG. 1, from the CT images I2 and I3 as well as the motion model M2. The image I4 contains substantially the same motion artifacts as a PET image which is reconstructed without any attenuation information. As a result, the motion artifacts in the PET image are taken into account and the reconstruction R5 using the attenuation information from the image I4 produces a qualitatively enhanced image I10 in comparison with a reconstruction utilizing a conventional transmission image.

Generally speaking, the methods of the FIGS. 1, 2 and 3 can also be simultaneously used in a system so as to enable presentation of the various results of the methods to a viewer. The method of FIG. 3 can be combined at will with the methods of FIG. 1 and FIG. 2, that is, for as long as the system used is a combination system, because the co-ordinate systems of the PET system correspond substantially to those of the CT system only in the case of a combination system.

It is to be noted again that the methods shown in FIG. 1, FIG. 2 and FIG. 3 are not limited to CT and PET. For example, it is possible to acquire the image I0 by means of magnetic resonance tomography instead of a PET-based method or, alternatively, to acquire the images I2 and I3 by means of ultrasound or fast magnetic resonance tomography instead of by means of a CT-based method. Because the method in accordance with the invention in general offers a possibility for comparing images containing different information on a moving object, while taking into account motion artifacts present in an image, applications outside the medical field are also feasible. For example, an image of a traveling car which contains motion artifacts can be acquired by means of a thermal-sensitive camera and further images can be acquired by means of customary photographic methods. The image of the thermal-sensitive camera shows location-specific functional processes, whereas the photographic images represent structural features of the object. The superposition of such different types of information so as to form a combination image while taking into account the motion artifacts advantageously enables the presentation of all information simultaneously to a viewer.

The invention has been described with reference to the referred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method comprising:
    acquiring first modality image data while an imaged object moves over a range of motion and reconstructing the first modality image data into a motion artifacted first modality image, the first modality image being one of a positron emission tomography (PET) image or a single positron emission computed tomography (SPECT) image;
    acquiring second modality image data and reconstructing the second modality image data into second modality images which represent the object in respective states of motion with as few motion artifacts as possible, the second modality images being one of computed tomography (CT) images and magnetic resonance (MR) images;
    from the second modality images, determining a motion model which characterizes states of motion assumed by the object while moving through the states of motion;
    forming an intermediate image of the object from the motion model and the second modality images, the intermediate image representing the object as if it had moved during the acquiring of the second modality image data over the range of motion over which the object moved as the first modality imaging data was acquired, forming the intermediate image includes:
        forming other images of other states of motion of the object from the second modality image data;
        weighting and subsequently superimposing the other images and the second modality images in conformity with a frequency at which each of the other states of motion were assumed by the object while moving over the range of motion while the first modality image data was acquired;
    forming a combination image from the intermediate image and the first modality image.

2. The method as claimed in claim 1, wherein determining the motion model includes:
    determining a respective motion vector field for parts of the object.

3. The method as claimed in claim 1, further including:
    elastically registering the intermediate image and the first modality image prior to the formation of the combination image.

4. The method as claimed in claim 1, further including:
    focusing the combination image.

5. An image processing system which includes a data processing unit for carrying out the method as claimed in claim 1.

6. A medical examination apparatus, the apparatus including:
    a device for forming images or projections by means of a first imaging method;
    a second device for forming images or projections by means of a second imaging method;
    an image processing system that includes a data processing unit for carrying out the method as claimed in claim 1.

7. A computer readable medium containing instructions for controlling a data processing unit in such a manner that the data processing unit can carry out the method as claimed in claim 1.

8. A method of enhancing a first image of a moving object, the first image containing motion artifacts, the first image being a positron emission tomography (PET) image or a single positron emission computed tomography (SPECT) image, the method including:
    a. acquiring further images that represent the object in respective states of motion with as few motion artifacts as possible, the further images being one of computed tomography (CT) images and magnetic resonance (MR) images;
    b. from the further images, determining a motion model that characterizes the states of motion assumed by the object;
    c. forming additional images of others of the states of motion of the object from the further images and the motion model;
    d. weighting and subsequently superimposing the other images and the second modality images in conformity with a frequency at which each of the other states of motion were assumed by the object while moving over the range of motion over which the first modality image data was acquired; and
    e. focusing the first image by means of the motion model.

9. The method as claimed in claim 8, further including:
   registering the focused image and at least one of the f/rther images; and
   forming a combination image from the focused first image and the at least one of the further images.

10. The method as claimed in claim 8, wherein determining the motion model includes:
    determining a respective motion vector field for parts of the object.

11. A method of enhancing information contents of a first image of a moving object, to be reconstructed from projections acquired as the object moves over a plurality of states of motion and containing motion artifacts, the first image being a positron emission tomography (PET) image or a single positron emission computed tomography (SPECT) image, which method includes:
   a. acquiring further images that represent the object in at least two of the states of motion with as few motion artifacts as possible, the further images being one of computed tomography (CT) images and magnetic resonance (MR) images;
   b. from the further images, determining a motion model that characterizes the states of motion assumed by the object while the projections are acquired;
   c. forming additional images of others of the states of motion of the object from the further images and the motion model;
   d. weighting and subsequently superimposing the other images and the second modality images in conformity with a frequency at which each of the other states of motion were assumed by the object while moving over the range of motion at which the first modality image data was acquired;
   e. forming at least one intermediate image of the object from the motion model and the further images, the at least one intermediate image representing one or more of the states of motion assumed by the object while the projections are acquired;
   f. reconstructing the first image from the projections of the object and the at least one intermediate image.

12. The method as claimed in claim 11, wherein determining the motion model includes:
    determining a respective motion vector field for parts of the object.

13. A method of motion compensation comprising:
   acquiring a first sequence of image data of a moving object by a first imaging modality data acquisition system, the first imaging modality data acquisition system including one of a positron emission tomography (PET) system and a single positron emission computed tomography (SPECT) system;
   acquiring a second sequence of image data of the moving object by a second imaging modality data acquisition system, the second imaging modality data acquisition system including a computer tomography (CT) system, an ultrasound system, or a fast magnetic resonance (MR) tomography system;
   determining a motion model related to periodic motion of the object based on the second sequence of image data;
   forming other images of other states of motion of the object from the second modality image data;
   weighting and subsequently superimposing the other images and the second modality images in conformity with a frequency at which each of the other states of motion were assumed by the object while moving over the range of motion while the first modality image data was acquired;
   using the determined motion model, generating from the first sequence of image data a first modality image data set in a selected motion state.

14. The method as claimed in claim 13, further including:
    generating a combined image data set in the selected motion state from the first modality image data set and a second modality image data set in the selected motion state.

15. The method as claimed in claim 13, further including:
    registering coordinates systems of the first and second imaging modality data acquisition systems.

16. The method as claimed in claim 13, further including:
    sensing motion of the object at least during acquisition of the second sequence of imaging data.

17. The method as claimed in claim 16, wherein the sensed motion is a cyclic motion in which the object cyclically assumes each of a plurality of motion states.

18. The method as claimed in claim 13, wherein the motion model includes a motion vector field which indicates movement between at least two motion states.

19. An imaging system comprising:
   a first imaging modality data acquisition system for generating a first imaging modality sequence of image data, the first imaging modality being one of PET and SPECT;
   a second imaging modality data acquisition system for generating a second imaging modality sequence of image data, the second imaging modality being one of computed tomography ultrasound, and magnetic resonance;
   a motion sensor for sensing object motion;
   a processor programmed to:
     reconstruct the first modality image data into a motion artifacted first modality image;
     reconstruct the second modality image data into second modality images which represent the object in respective states of motion with as few motion artifacts as possible;
     from the second modality images, determine a motion model which characterizes states of motion assumed by the object while moving through the states of motion;
     form an intermediate image of the object from the motion model and the second modality images, the intermediate image representing the object as if it had moved during the acquiring of the second modality image data over the range of motion over which the object moved as the first modality imaging data was acquired, forming the intermediate image including:
       forming other images of other states of motion of the object from the second modality image data,
       weighting and subsequently superimposing the other images and the second modality images in conformity with a frequency at which each of the other states of motion were assumed by the object while moving over the range of motion while the first modality image data was acquired;
     form a combination image from the intermediate image and the first modality image.

20. The imaging system as claimed in claim 19, wherein the motion model characterizes motion states assumed by the object while moving among a plurality of motion states.

21. The imaging system as claimed in claim 19, further including:
    operating mathematically with the motion model to transform the first imaging modality image data to a selected motion state.

* * * * *